United States Patent [19]

Shen

[11] Patent Number: 4,773,254

[45] Date of Patent: Sep. 27, 1988

[54] AUTOMATED STEADY STATE RELATIVE PERMEABILITY MEASUREMENT SYSTEM

[75] Inventor: Joseph J. S. Shen, Brea, Calif.

[73] Assignee: Chevron Research Company, San Francisco, Calif.

[21] Appl. No.: 70,760

[22] Filed: Jul. 7, 1987

[51] Int. Cl.[4] .......................................... G01N 15/08
[52] U.S. Cl. ..................................................... 73/38
[58] Field of Search ........................................... 73/38

[56] References Cited

U.S. PATENT DOCUMENTS

| | | | |
|---|---|---|---|
| 3,018,660 | 1/1962 | Schmid | 73/38 X |
| 3,023,606 | 3/1962 | Sarem | 73/38 |
| 4,390,842 | 6/1983 | Wygent et al. | 324/439 |
| 4,420,975 | 12/1983 | Nagel et al. | 73/155 |
| 4,486,714 | 12/1984 | Davis et al. | 324/376 |
| 4,487,056 | 12/1984 | Wiley | 73/38 |
| 4,506,542 | 3/1985 | Rose | 73/38 |
| 4,561,289 | 12/1985 | Jones | 73/38 |
| 4,573,342 | 3/1986 | Jones | 73/38 |
| 4,643,019 | 2/1987 | Jones | 73/38 |
| 4,649,737 | 3/1987 | Jones | 73/38 |

OTHER PUBLICATIONS

XERTEX Product Data Sheet (1983) "Continuous Liquid Level Transmitter for Sight Gauge, Standpipe, and Small Tank Installations.
Drexel Engineering Company "Universal Lever Transmitter Data Sheet, (1981).
F. N. Schneider et al., "Steady-State Measurement of Relative Permeability for Polymer/Oil Systems" (Feb. 1982).
F. F. Craig, Jr., 'The Reservoir Engineering Aspects of Waterflooding", SPE of AIME (1971).
D. J. O'Meara, Jr., et al., "Multiphase Relative Permeability Measurements Using an Automated Centrifuge" SPE 121228 (1983).
S. C. Jones, et al., "Graphical Techniques for Determining Relative Permeability From Displacement . . . " SPE of AIME (5/1978).
T. E. Miller, Jr., et al., "Thermal Pulse Time-of-Flight Liquid Flow Meter" Anal Chem 1982 54, 907–910.

Primary Examiner—Michael J. Tokar
Assistant Examiner—Joseph W. Roskos
Attorney, Agent, or Firm—S. R. La Paglia; E. J. Keeling; V. A. Norviel

[57] ABSTRACT

An automated method of determining relative permeability is described comprising the steps of injecting known flow rates of water and a hydrocarbon into a core; measuring a pressure differential across the core; flowing the water and the hydrocarbon into a water-hydrocarbon interface measuring column; monitoring an interface level in the column with an ultrasonic probe, and calculating relative permeability with an automated device based on the pressure differential and the interface level.

2 Claims, 3 Drawing Sheets

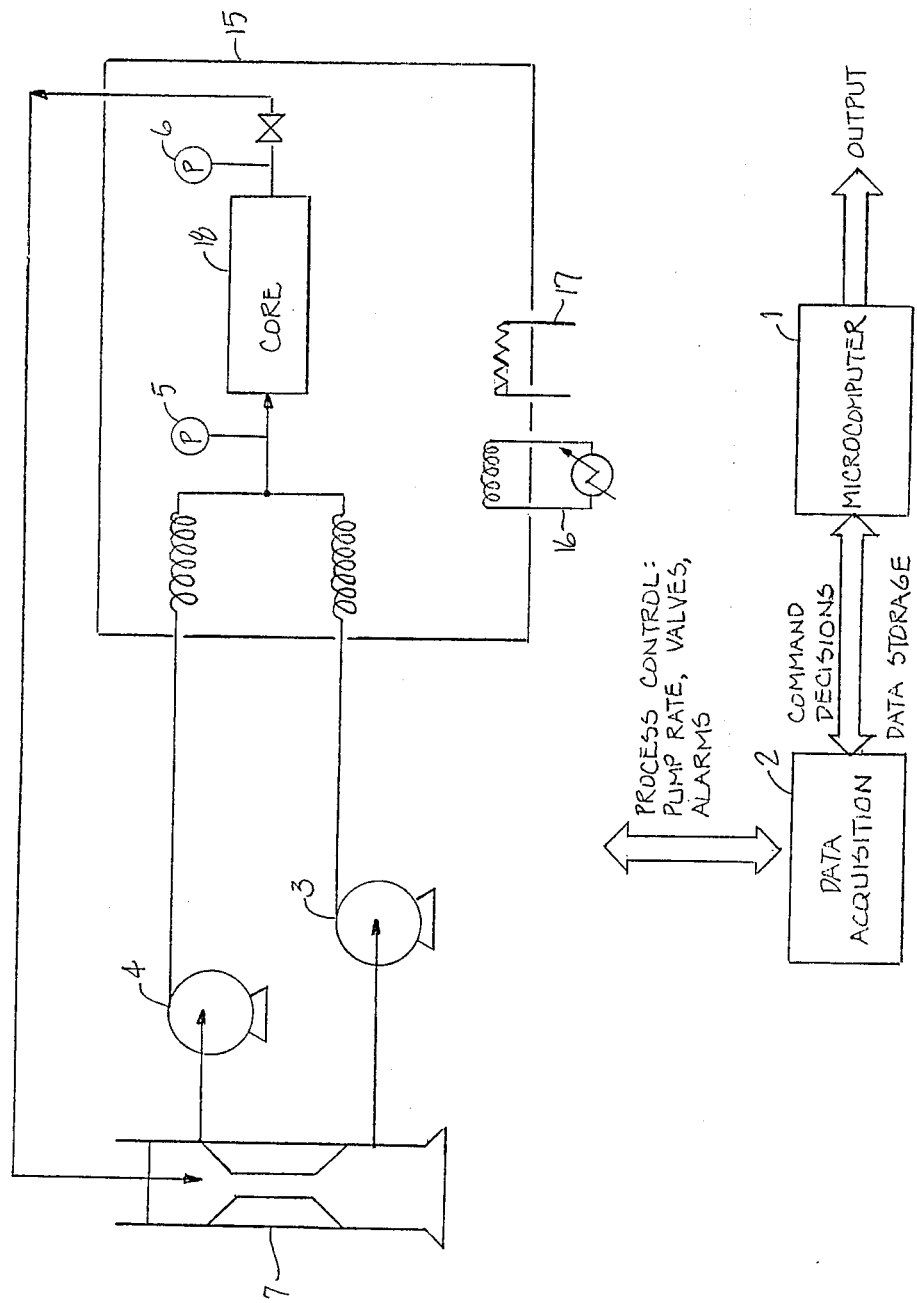
FIG._1.

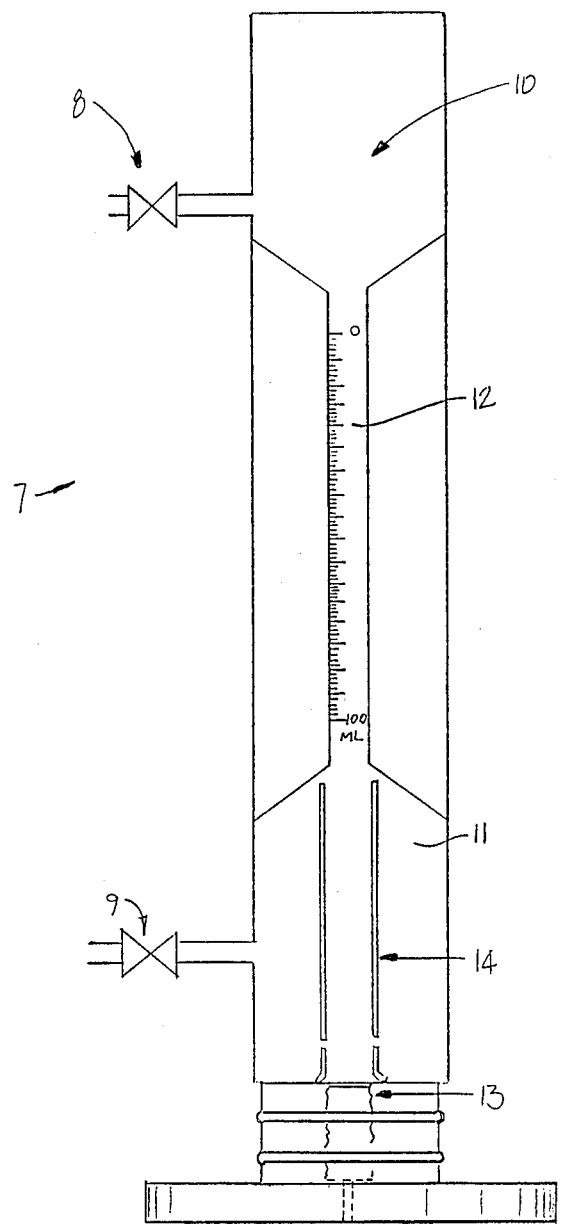
FIG_2.

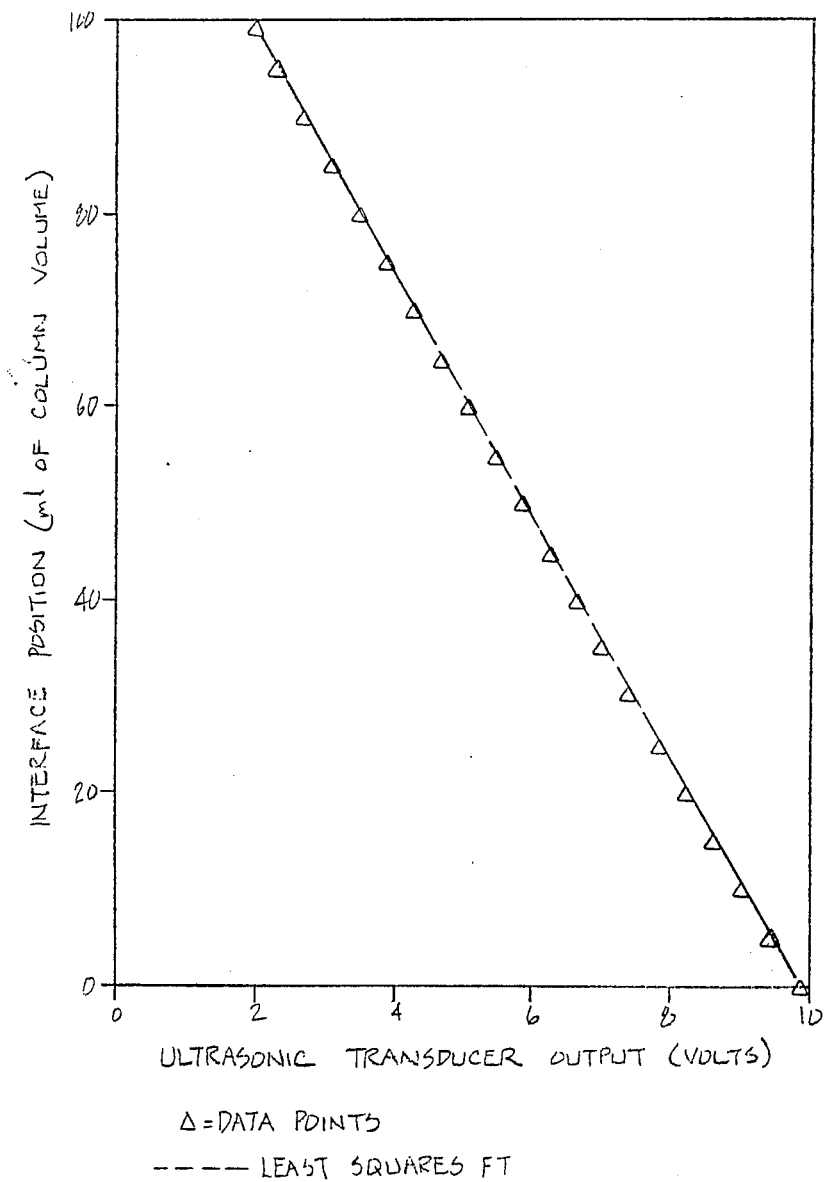
FIG._3.

AUTOMATED STEADY STATE RELATIVE PERMEABILITY MEASUREMENT SYSTEM

FIELD OF THE INVENTION

The present invention relates to laboratory devices used to measure the relative permeability of reservoir rocks. In particular, the present invention provides an improved, automated method of determining permeability using an ultrasonic probe.

BACKGROUND OF THE INVENTION

Water and oil relative permeabilities of reservoir rocks are routinely needed in the analysis of a waterflood and enhanced oil recovery projects. Such data are, for example, required in almost all flow and recovery calculations. Among various ways to measure relative permeabilities, the so-called steady-state method and transient method are the two most common techniques. The transient method (also known as displacement or "Welge" method) is easy and efficient. However, useful data are obtained only when the displacing fluid is more mobile than the displaced fluid. Therefore, imbibition relative permeabilities of a water-wet rock can be generated with water displacing oil but good drainage curves cannot be obtained with oil displacing water. Furthermore, displacement tests with an unfavorable mobility ratio may be plagued by viscous fingering problems.

By contrast, the steady-state method can be used to obtain accurate relative permeabilities for either oil wet or water wet rocks. In the steady-state method, water and oil are injected simultaneously in known relative amounts into a core. Pressure differential across the core during flow is measured. After fluid saturations within the test core have reached equilibrium, the saturations are determined by one of many techniques such as gravimetrical, electrical resistivity, X-ray or microwave absorption. One simple technique to determine fluid saturations involves recycling of the water and oil from the core into a holding tank. By noting the rise and fall of the water-oil interface inside the holding tank, changes of fluid saturations inside the test core may be calculated by a simple material balance.

The experimental apparatus and procedures for steady-state relative permeability measurements are thus straightforward. There is, however, a major drawback. The steady-state method is time-consuming and tedious. It may take quite a while to reach a steady state at each pump setting, especially in the neighborhood of residual saturations. Meanwhile, an operator's attention is required to record the data and to determine if an equilibrium has been attained. For this reason, the steady-state method is not as widely used as the transient method for measuring two-phase relative permeabilities although it is the surest way to obtain correct results. To date, however, there has not been a satisfactory method of automating the system.

Early attempts at making automated relative permeability measurements have resulted in complex and, often, unworkable devices. For example, one automated system recently developed for relative permeability measurement was based on a centrifuge technique (D. S. O'Meara, Jr., et al., SPE Paper 12128, "Multiphase Relative Permeability Measurements Using an Automated Centrifuge", 1983). It has been found that this method is unsatisfactory because it requires spinning down the oil-water mixture in the core while "pictures" are taken of the spinning core. This can be time consuming, complex and, therefore, prone to failure. It is clear that an improved automated relative permeability measuring system is needed.

SUMMARY OF THE INVENTION

An automated method of determining relative permeability is described comprising the steps of injecting known flow rates of water and a hydrocarbon into a core; measuring a pressure differential across said core; flowing said water and said hydrocarbon into a water-hydrocarbon interface measuring column; monitoring an interface level in said column with an ultrasonic means; and calculating relative permeability with an automated means based on said pressure differential and said interface level. An automated apparatus for determination of relative permeability in cores is also described comprising a means for injecting water and a hydrocarbon bearing oil into a means for holding a subterranean core sample, said means for pumping capable of injecting precisely known flow rates of oil and water; means for measuring pressure differential across said means for holding a core; means for flowing water and oil to a water-oil interface level measuring column; an ultrasonic means for measuring the interface level in said column; means for monitoring said pressure differential, said known flow rates of oil and water, and said interface level; and means for automatically calculating relative permeability of a core operably connected to said means for monitoring.

DESCRIPTION OF THE DRAWINGS

FIG. 1 is a simplified flow diagram illustrating the apparatus for measuring relative permeability.

FIG. 2 illustrates the column illustrated in FIG. 1 in greater detail.

FIG. 3 provides a calibration curve for a water-oil interface in a glass column with an ultrasonic probe.

DETAILED DESCRIPTION OF THE INVENTION

With reference to FIG. 1, the apparatus has a means for holding a core 18 of the type well known in the art. Pumps 3 and 4 are used to inject oil, or any suitable hydrocarbon substance into the core and holder 18 in known amounts. Pressure monitoring means 5 and 6 are used to measure the pressure at each end of the core and/or the differential pressure across the core. After fluid saturations in the core have reached equilibrium the saturation is determined by recycling the water and oil from the core into holding column 7. The water and oil interface is monitored using ultrasonic probe transmitter 13. By means of simple mass balance calculations the relative permeability of the core can then be determined.

The data acquisition and process control system is shown schematically in FIG. 1. In general input signals of pressure-drop and interface level are logged and fed to a computer data acquisition unit 2 and computer 1. The computer records these data and determines if a steady-state condition has been reached. Once the core is deemed in equilibrium, the process controller then changes the signal output to the pumps 3 and 4 to effect a different combination of water-oil injection rates. All measurements are taken in a temperature controlled bath 15 which has a cooling element 16 and a heating element 17.

Pumps 3 and 4 must have constant flow rates with time. The pumps must also be externally-controllable for automation. In the preferred embodiment, Milton-Roy's Constametric dual-piston positive displacement pumps are used as the water and oil injection pumps. They are rated at 10 ml/min and 5000 psig. These pumps are also equipped with 0-10 VDC analog outputs for the flow rate and discharge pressure. External control of the pump flow rate is effected through a 0-5 VDC input. Pre-selected pump settings may be checked manually before a run, or low-rate flow meters may be utilized such as the Thermapulse liquid flow meter.

Pressure differential measurements are obtained with conventional pressure transducers e.g., 5 and 6, made by Validyne in a preferred embodiment. Transducer diaphragms are calibrated against known gas pressures before each run. Analog signals of 0-10 VDC are recorded on a strip chart recorder.

A micro-computer 1 with dual-disc drive (an HP 9816S in the preferred embodiment) is used to automate the device. The computer interfaces with other computer components (data acquisition and control unit 2, printer, disc drive) through an HP-IB bus. Digital voltage signals received from the data acquisition unit are converted into appropriate physical units. Pressure measurements are scaled from diaphragm calibrations. Temperatures are obtained by converting thermocouple voltages via a 9th order polynomial regression formula. The water-oil interface level in the holding tank is obtained by linear regression analysis correlating the transducer voltage and water column height.

A Hewlett-Packard 3497A is used as the data acquisition unit 2 for the system. Two plug-in cards are installed. A 20-channel relay multiplexer assembly is used for analog input and a dual channel, 0 to 10 V D/A converter is used for analog output. A total of 15 channels are used in the multiplexer assembly. They include 8 pressure measurements: water and oil pump discharge pressures, water and oil line pressures at the core inlet, core sleeve pressure, two differential pressures across the test core (a high and a low diaphragm), and core outlet pressure. Four J-type thermocouples (not shown) are used in the system: water and oil line temperatures at core inlet, oven temperature, and the room temperature. Three additional inputs include two pump flow rates from the pump's electronic circuits rather than actual flow measurements) and transducer output from the level detector.

Column 7 is used to monitor an oil-water interface and is shown in more detail in FIG. 2. Chamber 7 comprises an oil outlet 8, water outlet 9 associated with oil and water chambers 10 and 11, respectively. A graduated column 12 provides a visual indication of an oil water interface. An ultrasonic transmitter 13 is located at the bottom of the column, and monitoring is accomplished by non-contact ultrasound transmission through the medium. A Continuous Liquid Level Transmitter by Xertex is used in the preferred embodiment. Reflected ultrasound signals are filtered to eliminate detection of a secondary oil-air interface. A conduit 4 is installed over the probe to guide the waves into the narrow column. The water-oil surface interface is maintained within the graduated column 12 between the oil and water chambers for accurate reading of volume changes. The column volume of the tank is graduated from 0 (at the top) to 100 in 0.2 ml markings.

Although the ultrasonic probe actually measures the height of the interface from a baseline, it is easier to calibrate the transducer output (2-10 VDC) in terms of the fluid volume in the column. The transducer voltage is calibrated over a 100 ml fluid volume change as shown in FIG. 3. Excellent linearity and reproducibility are seen. With least-square analysis of the calibration data, the position of the water-oil interface inside the 100 ml connecting column can be detected quite accurately, usually with 0.8 ml.

The permeability of a core is generally computed by using the Darcy's law which for horizontal, linear flow of an incompressible fluid can be stated as:

$$K = \frac{q \mu L}{A \, dP}$$

where K is permeability in the unit of Darcy, q is fluid flow rate in cubic centimeter/sec., $\mu$ is fluid viscosity in centipoise, L is the length of the test core in centimeters, A is the cross-sectional area of the test core in square centimeters, and dP is the pressure drop across the core in atmospheres.

When only a single fluid (phase) flows inside the core, the computed permeability is called the absolute permeability which is easily determined by workers versed in this art. When two or more phases, such as a hydrocarbon phase and an aqueous phase, flow concurrently in the core, the same Darcy's law can still be applied by using respective values of flow rate and viscosity for each phase in the above equation. The calculated permeability for each phase is called its effective permeability. Relative permeability of a phase is then simply the dimensionless value of dividing the effective permeability of that phase by the absolute permeability.

While the absolute permeability of a core is a constant value, the effective permeabilities, hence, the relative permeabilities, are not constant. They depend on the saturation value of each phase inside the core. Thus, relative permeability values are meaningful only if stated with saturations because they vary with changing saturation. Saturation of a phase is simply the fraction of the pore space occupied by that phase. For example, for a core of 100 cc of pore volume, containing only a hydrocarbon and an aqueous phase, a water saturation of 0.40 means that water occupies 40 percent of the pore volume or 40 cc. It also follows that oil occupies the other 60 percent of the pore volume for an oil saturation of 0.60.

By continuously monitoring the rise and fall of the water-hydrocarbon interface level in the recycle tank as taught in the present invention, the saturation of each phase in the core, which is connected to the recycle tank, can be calculated continuously during the test. For example, at one particular flow rate setting during the test for a core of 100 cc of pore volume, the water-hydrocarbon interface level in the recycle tank is noted to have risen by 10 cc compared to the interface level during the previous pump rate setting. It means 10 cc of water has entered the recycle tank because the hydrocarbon phase generally floats above the aqueous phase in the recycle tank. In a closed system, this 10 cc of water entering the recycle tank can only come from the core material being tested. By material balance, it follows that 10 cc of hydrocarbon has left the recycle tank and entered the core to replace the 10 cc of water that has exited. Therefore, the saturation of the aqueous phase inside the core is reduced by 0.1 (10 cc/100 cc of pore volume) and the saturation of the hydrocarbon phase is increased by the same 0.1 pore volume when compared with the saturation of each phase during the previous pump rate setting. Conversely, a fall of the water-hydrocarbon interface level in the recycle tank means that water has left the tank and entered the core. Consequently, the water saturation in the core increases and the hydrocarbon saturation decreases.

The automated relative permeability measurement system taught in this invention, thus, involves continuously measuring or knowing the pressure drop and the hydrocarbon and water flow rates so that the effective permeability of each phase can be calculated by the Darcy's law while other physical variables in the above equation such as the cross-sectional area and length of the core and the viscosity of each fluid and the absolute permeability can be determined independently. The saturation of each phase inside the core at which the relative permeabilities are measured are then calculated as illustrated above the continuously monitoring the water-hydrocarbon interface level in the recycle tank by an ultrasonic means.

Although the invention has been described with a great deal of particularity, variations on the idea will be readily apparent to one skilled in the art. For example, the ultrasonic probe may also find applications in other experiments, such as core recovery tests. The cumulative amount of oil being recovered can be monitored continuously as the flood progresses. The host computer can calculate other parameters of interest such as the instantaneous oil production rate and oil/water cut.

Another example where the probe may be used is in relative permeability measurements by the transient method. In the transient method, waterflood of a (viscous) oil-saturated core is conducted. The transient method is thoroughly described in Jones et al., J. Petroleum Technology, May 1978, page 807-17, which is incorporated by reference herein for all purposes. From the pressure drop and oil recovery data relative permeability curves can be constructed. In this case, the experimental system developed can be used just as in the steady-state runs except the oil pump is not used. The real-time data so obtained can be incorporated directly into a previously developed computer program, employing a graphical analysis technique to calculate the relative permeabilities. While the transient method is already quite efficient as mentioned before, automated data-taking and computerized analysis described here should enhance the productivity and accuracy even further. Therefore, the scope of the invention should be determined not with reference to the above description but instead with reference to the appended claims along with the full scope of the equivalents thereto.

What is claimed is:

1. An automated method of determining relative permeability comprising:
    (a) pumping a single phase hydrocarbon through a core while measuring a first differential pressure across said core;
    (b) calculating an absolute permeability of said core to said hydrocarbon;
    (c) pumping a known water volume and a known hydrocarbon volume into said core;
    (d) measuring a second pressure differential across said core;
    (e) flowing said water and said hydrocarbon into a water-hydrocarbon interface measuring column;
    (f) monitoring an interface level in said column with an ultrasonic means;
    (g) calculating a saturation of hydrocarbon in the core based on said interface level; and
    (h) calculating relative permeability with an automated means based on said pressure differential and, said permeability of said core to said hydrocarbons at said saturation.

2. The method as recited in claim 1 further comprising the step of controlling a temperature of said core.

* * * * *